US008690901B2

(12) United States Patent
Schulze

(10) Patent No.: US 8,690,901 B2
(45) Date of Patent: *Apr. 8, 2014

(54) ARRANGEMENT AND METHOD FOR VASCULAR ANASTOMOSIS

(75) Inventor: Dale R. Schulze, Lebanon, OH (US)

(73) Assignee: Ethicon, Inc., Somerville, NJ (US)

( * ) Notice: Subject to any disclaimer, the term of this patent is extended or adjusted under 35 U.S.C. 154(b) by 778 days.

This patent is subject to a terminal disclaimer.

(21) Appl. No.: 12/251,182

(22) Filed: Oct. 14, 2008

(65) Prior Publication Data
US 2009/0043298 A1 Feb. 12, 2009

Related U.S. Application Data

(63) Continuation of application No. 11/069,025, filed on Feb. 28, 2005, now abandoned, which is a continuation of application No. 09/966,971, filed on Sep. 28, 2001, now Pat. No. 6,860,891.

(51) Int. Cl.
A61B 17/08 (2006.01)

(52) U.S. Cl.
USPC .......................................................... 606/153

(58) Field of Classification Search
USPC ............ 606/139, 144–156, 222–231; 600/36; 623/1.13, 1.23; 128/898
See application file for complete search history.

(56) References Cited

U.S. PATENT DOCUMENTS

| 3,019,789 A | 6/1958 | Whitehill et al. |
| 3,123,077 A | 3/1964 | Alcamo |
| 4,368,736 A | 1/1983 | Kaster |
| 4,657,019 A | 4/1987 | Walsh et al. |
| 5,041,127 A | 8/1991 | Troutman |
| 5,486,187 A | 1/1996 | Schenck |
| 5,695,504 A | 12/1997 | Gifford, III et al. |
| 5,817,113 A | 10/1998 | Gifford, III et al. |
| 5,868,763 A | 2/1999 | Spence et al. |
| 5,893,369 A * | 4/1999 | LeMole .................... 606/184 |
| 5,944,730 A | 8/1999 | Nobles et al. |
| 5,972,024 A * | 10/1999 | Northrup et al. ............ 606/232 |
| 5,976,159 A | 11/1999 | Bolduc et al. |
| 6,015,416 A | 1/2000 | Stefanchik et al. |
| 6,391,038 B2 * | 5/2002 | Vargas et al. ................. 606/153 |
| 6,551,332 B1 * | 4/2003 | Nguyen et al. ............... 606/151 |
| 6,860,891 B2 * | 3/2005 | Schulze ....................... 606/153 |
| 2001/0018592 A1 | 8/2001 | Schaller et al. |
| 2002/0103459 A1 * | 8/2002 | Sparks et al. ............. 604/164.13 |
| 2002/0143347 A1 * | 10/2002 | Cole et al. .................... 606/153 |
| 2003/0023253 A1 | 1/2003 | Vargas et al. |
| 2003/0028205 A1 | 2/2003 | Vargas et al. |

FOREIGN PATENT DOCUMENTS

| EP | 0 314 412 | 5/1989 |
| WO | WO 98/37218 | 7/1999 |

* cited by examiner

Primary Examiner — Melanie Tyson

(57) ABSTRACT

A method for implementing vascular anastomosis in the attachment of a graft vessel to a target vessel such as a coronary artery, and subsequently creating a passageway between the vessels in order to establish fluid flow communication therebetween. Further is to the provision of novel devices which are utilized in implementing the steps of attaching a graft vessel to a target vessel such as a coronary artery through vascular anastomosis, and thereafter creating a fluid flow passageway therebetween.

14 Claims, 9 Drawing Sheets

ARRANGEMENT AND METHOD FOR VASCULAR ANASTOMOSIS

CROSS REFERENCE TO RELATED APPLICATION

This application is a continuation of U.S. application Ser. No. 11/069,025 filed Feb. 28, 2005, which is a continuation of U.S. Pat. No. 6,860,891 granted Mar. 1, 2005, the entire contents of which are incorporated herein by reference.

BACKGROUND OF THE INVENTION

1. Field of the Invention

The present invention relates to a method for implementing vascular anastomosis in the attachment of a graft vessel to a target vessel such as a coronary artery, and subsequently creating a passageway between the vessels in order to establish fluid flow communication therebetween. The invention is further directed to the provision of novel devices which are utilized in implementing the steps of attaching a graft vessel to a target vessel such as a coronary artery through vascular anastomosis, and thereafter creating a fluid flow passageway therebetween.

The concept of anastomosis in implementing the attachment of target vessels, for instance, such as coronary arteries and other body vessels which are subjected to a fluid flow, such as blood to a graft vessel which is intended to be placed in fluid flow communication with the target vessel is well known in the medical technology.

Quite frequently, the attachment or anastomosis of the vessels is implemented through the intermediary of hand suturing of the graft vessel to the target vessel, in effect the coronary artery, necessitating the carrying out of extremely difficult and highly dangerous surgical procedures.

Generally a surgeon will perform an arteriotomy on the coronary artery at a location which is downstream from a blockage; however some flow of blood may still be present in the diseased artery. Occasionally the blood flow through the artery is temporarily occluded by means of a clamp in order to be able to incise the coronary and then perform the anastomosis with a minimal blood leakage. Nevertheless, the occluding of the artery occasionally dislocates plaque which lines the intima of the diseased coronary artery, enabling the plaque particles to migrate downstream, and thereby creating a scenario for the propagation of subsequent complications over time which may be readily life threatening to a patient. Even in the event that the coronary artery is occluded prior to the arteriotomy, it is usually necessary to manage any blood leakage which may be encountered by means of a $CO_2$ blower. Thus, it may be advantageous to be able to perform the anastomosis of the graft vessel to the coronary artery or any target vessel without first having to implement an arteriotomy on the target vessel or coronary artery.

Moreover, the cardiac surgeon must exercise considerable care in order to stitch the intima of the graft vessel to the intima of the coronary artery in order to promote healing at the location of the passage way which has been created between the newly joined graft vessel and the coronary artery. In an ideal situation, the cardiac surgeon intends that the edges of the incision of one vessel are to be perfectly aligned with the mating or opposite edges of the incision of the other vessel, enabling endothelial tissue to quickly form a smooth seam joining the vessels with a minimum build-up of intraluminal tissue mass which may conceivably restrict blood flow subsequent to the joining of the vessels. A conventional stitching method using a running suture also may result in so-called purse stringing or bunching of tissue at various locations along the perimeter of the anastomosis, with the resulting potential of creating subsequent occlusions at those locations. In addition to the foregoing, cardiac surgeons presently slice the coronary artery with a small scalpel, at times utilizing a large number of strokes in order to cut through layers of the interior walls of the artery, and by approximating the length of the incision required based on the size of the graft vessel. This necessitates extreme care to be exercised in order to avoid cutting the posterior wall of the artery.

Consequently, it is imperative that methods and apparatus be developed for forming an anastomosis of a graft vessel to a coronary artery or similar target vessel without first having to create an arteriotomy on the target vessel or artery. Moreover, also desirable is to be able to join the vessels in an anastomosis prior to creating a passageway facilitating fluid flow therebetween in order to ensure that the opposing edges of the incisions in the graft and target vessels are perfectly aligned and stabilized, and with the avoidance of any purse stringing or bunching of the tissues along the anastomosis perimeter. It is also necessary that a method be developed for incising the artery without the possibility of such posterior wall cuts having to be implemented, and with only a minimal chance of rendering the incisions to be either too lengthy or too short at the location of the anastomosis.

It has also been ascertained that bio-adhesives may be utilized in the joining together or anastomosis of blood vessels; however, in the event that an arteriotomy is implemented prior to adherence between the vessels, it is a possibility that the surgeon may inadvertently apply adhesive material onto the intima of the vessels which are to be joined, thereby impeding the appropriate healing of the joined vessels. Thus, there is a need for a method which will alleviate this potential danger to the patient in being able to join the vessels without exposing the intima of either vessel to the bio-adhesive.

2. Discussion of the Prior Art

Although numerous publications are currently available which to varying degrees concern themselves with this particular technology, none of them clearly or satisfactorily provide teachings regarding vascular anastomosis methods or devices which will provide for the joining of a target vessel, such as a coronary artery, to a graft vessel prior to the cutting of a fluid flow passageway between the graft vessel and the target vessel so as to generally, to a considerable degree, alleviate the difficulties and shortcomings encountered in the medical technology.

Nobles et al. U.S. Pat. No. 5,944,730 discloses a device and method for assisting in end-to-side anastomosis wherein a sealing device pierces the one vessel and then forms a inner seal around an inner wall of an incision in an arterial blood flow or target vessel. Thereafter, a graft vessel is attached to the target vessel or artery, and appropriate suturing implemented, whereupon the seal is then withdrawn through the graft vessel providing for fluid or blood flow communication between the coronary artery and the graft vessel.

Stefanchik et al. U.S. Pat. No. 6,015,416 discloses an end-to-side anastomosis between two vessels, wherein a passageway is initially created between the vessels and thereafter a plow structure of a surgical anastomosis instrument is withdrawn subsequent to effectuating anastomosis therebetween.

Troutman U.S. Pat. No. 5,041,127 discloses an offset point surgical needle adapted to pierce through the walls of a vessel which is to be subjected to anastomosis with another vessel.

Whitehall et al. U.S. Pat. No. 3,019,789 discloses an anastomosis clamp for the intimal-to-intimal anastomosis of two vessels, and wherein sutures are to be applied to the location of the anastomosis subsequent to the formation of a flow passageway between the vessels.

The foregoing publications all entail the forming of passageways which permit blood flow between a coronary artery or target vessel and a graft vessel prior to anastomosis, and which are subject to the drawbacks and disadvantages described hereinabove.

Other publications also concern themselves with different types of devices and methods for performing anastomosis between blood vessels or graft vessels.

Bolduc et al. U.S. Pat. No. 5,976,159 discloses a surgical clip and method for tissue approximation, which enable the end-to-end anastomosis and method for tissue approximation, and which also enable the end to the side anastomosis between a coronary artery and a graft vessel subsequent to the forming of a flow passageway therebetween.

LeMole U.S. Pat. No. 5,893,369 describes a procedure for bypassing an occlusion in a blood vessel wherein an end-to-side anastomosis is performed between two vessels and wherein a graft vessel initially has a seal element punch a passageway through the target vessel or artery. Thereafter the graft vessel is attached thereto by means of suitable clamps, whereupon subsequent to suturing the seal element is withdrawn through the graft vessel.

Walsh et al. U.S. Pat. No. 4,657,019 describes an anastomosis device wherein forceps are adapted to engage ring shaped anastomosis elements in order to perform end-to-end anastomosis between a, artery or target vessel and a graft vessel. This also entails the formation of a flow passageway prior to carry out the anastomosis.

Gifford, III et al. U.S. Pat. No. 5,695,504 describes various methods and apparatus for performing anastomosis in an end-to-end and side vascular surgery, particularly coronary artery bypass surgery. In this instance, a passageway is formed in a target vessel or coronary artery wherein ring shaped anastomotic couplers are introduced through an incision formed therein and then connected to a graft vessel. This also entails forming a blood flow passageway between the vessels prior to the anastomosis thereof.

Similarly, Gifford, III et al. U.S. Pat. No. 5,817,113 discloses the formation of a flow communication in a target vessel, such as coronary artery, prior to anastomosis with a graft vessel.

Kaster U.S. Pat. No. 4,368,736 describes an anastomotic fitting for performing an end-to-side anastomosis between a target vessel, such as an aorta or coronary vessel, and a graft vessel. In that instance a passageway facilitating blood flow between the vessels is formed prior to the anastomosis which is implemented by way of surgical clips engaging the tissue of the target vessel.

Spence et al. U.S. Pat. No. 5,868,763 discloses an apparatus and method adapted to perform anastomosis, wherein side-to-side anastomosis between two vessels is implemented subsequent to the forming of a passageway between the vessels, which enables blood flow through the vessels prior to completing the anastomosis.

Finally, International Publication WO 99/37218 (PCT/US99/01182) provides a system for performing vascular anastomosis in which an opening is formed in a target vessel, such as a coronary artery, and subsequently an anastomosis is performed in the attachment of a graft vessel thereto.

All of the foregoing publications require the termination of blood flow through the target vessel during implementing of the foregoing procedures, or necessitate lengthy surgical procedures which includes considerable risk to patients and which are subject to high degrees of morbidity and potential mortality while necessitating lengthy hospital stays for the patient.

SUMMARY OF THE INVENTION

According to the present invention, the foregoing drawbacks and disadvantages are clearly obviated in that novel methods and devices for anastomosis between a coronary artery or target vessel and a graft vessel are implemented prior to the formation of a fluid flow passageway between the vessels, thereby enabling the maintaining of a continued blood flow during the anastomosis.

Pursuant to one aspect of the invention, the anastomosis is performed by inserting a suture wire through one wall of the target vessel or coronary artery, and then passing out the suture wire from that wall at a predetermined distance from the point of insertion, passing the opposite outwardly extending ends of the wire through a second vessel, such as graft vessel, positioning the graft vessel in close proximity to the coronary artery or target vessel and adhering the graft vessel to the target vessel at that particular location through diverse means. Prior to the formation of the fluid flow passageway between the two vessels, attachment is implemented at that location intermediate the wire ends by either the application of an adhesive, suturing, or a combination of adhesive and sutures, and thereafter withdrawing the wires while cutting a passageway therewith between the graft vessel and the target vessel or coronary artery within the confines of the anastomosis area, and thereafter removing the wire.

The foregoing passageway forming method for interconnecting the vessels in fluid flow communication may be implemented by the suture wire in that the wire is longitudinally reciprocated so as to form a kind of cutting blade in the form of a so-called "cheese cutter", or alternatively, the wire may have electrical energy applied thereto in a region defined by the juncture or anastomosis of the vessels, so as to essentially melt through the vessel tissues to thereby produce the passageway.

Accordingly, it is a primary object of the present invention to provide a novel method of implementing anastomosis between two body vessels prior to the formation of a fluid flow passage way therebetween at the location of the anastomosis.

Another object of the present invention is to provide a suitable suture wire extending through the location of the proposed anastomosis between two vessels, such as a graft vessel and a target vessel consisting of a coronary artery, whereby anastomosis is implemented and thereafter the suture wire is manipulated to cut through the vessels at the site of the anastomosis in order to form a blood flow passageway therebetween, and the effectuating removal of the suture wire.

Another object resides in the provision of an arrangement for implementing anastomosis between two body vessels which are in a generally side-to-side orientation, through the interposition of a suture wire extending into the vessels, and subsequently applying electrical energy or radio frequency energy to the wire so as to serve through the tissues separating the vessels at the location of the anastomosis, thereby forming a blood flow passageway between the vessels, and thereafter removing the suture wire.

BRIEF DESCRIPTION OF THE DRAWINGS

Other objects and advantages of the invention and novel features thereof may be readily ascertained from the following detailed description of the invention, taken in conjunction with the accompanying drawings; wherein.

DETAILED DESCRIPTION OF PREFERRED EMBODIMENTS

Figure 1A:
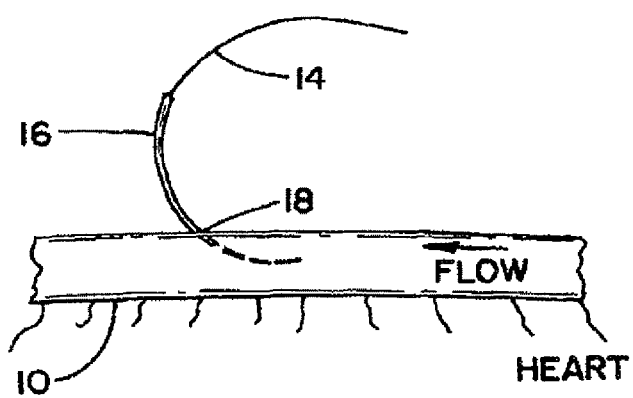
FIGS. 1a through 5 illustrate a first embodiment of a sequence in steps of performing anastomosis and subsequent forming of a fluid flow passageway between two body vessels.
Figure 1B:
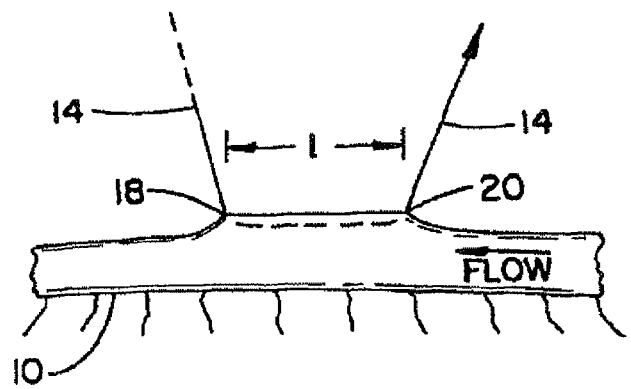

Referring now to a first embodiment of the anastomosis device and flow passage producing method, as indicated schematically in FIGS. 1a-5 of the drawings, there are represented successive steps in implementing a side-to-side anastomosis between a first body vessel 10, such as a coronary artery, and a second vessel 12 which may be a graft, and wherein the vessels 10, 12 are intended to be joined in an edge-to-edge contact rather than intima-to-intima contact. As shown in FIG. 1a of the drawings, a suture wire 14 having a suture needle 16, essentially of curved configuration attached at both ends thereof (only one shown) is inserted into the coronary artery 10 at a first location 18 by puncturing the vessel wall. As indicated in FIG. 1b of the drawings, the suture needle 16 at the leading end of the suture wire 14, is manipulated so as to exit the coronary artery 10 at a second generally axial or longitudinally distant point 20 located therefrom at a distance L, therefrom. The needles at both outer ends of the suture wire are drawn upwardly so as to essentially form the entry puncture and exit puncture distance L which will subsequently define the length of a fluid flow communication or aperture to be formed between the first and second vessels 10, 12; in effect, between the coronary artery and the graft vessel. In effect, when two hollow organs or vessels are joined side-to-side near a free closed end of one of the vessels, this is referred to as a functional end-to-side anastomosis. Thus, once an incision is made, as set forth pursuant to the invention, the fluid passageway created between the vessels eventually assume an approximately circular shape due to the pressure of the fluid flow in the vessels, and whereby the edge-to-edge approximation of the passageway perimeter is maintained so that healing may take place.

Figure 2:
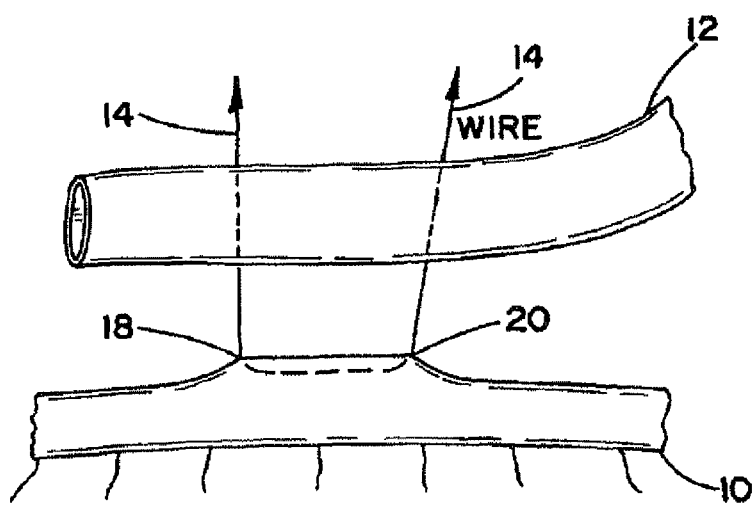

As shown in FIG. 2 of the drawings, each of the needles 16 at the opposite ends of the suture wire 14 (only one needle shown) is adapted to puncture through the wall second or graft vessel 12 at two locations which are essentially at a same spacing L as that in the coronary artery 10, and wherein the wire exit at the opposite located circumferential wall of the graft vessel 12 by passing through the latter.

Figure 3:
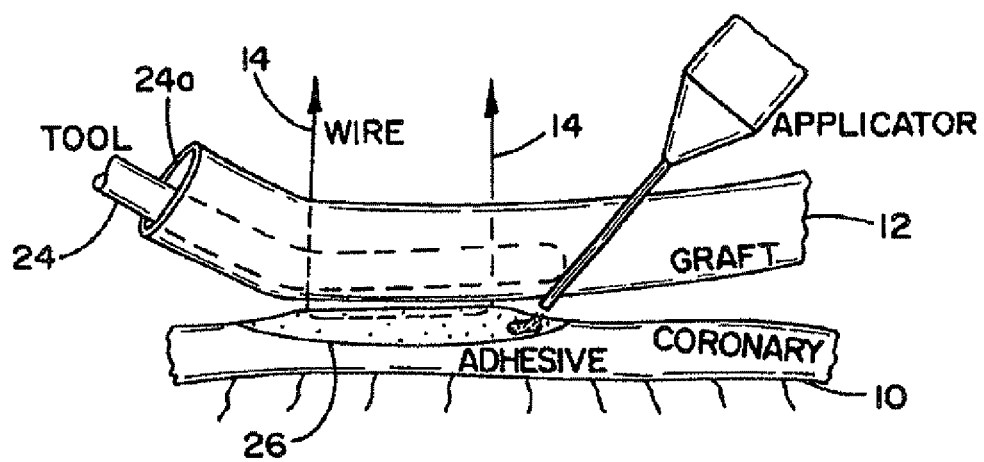

A tool 24 which may be the leading end of a rod-like member is inserted into an open end 24A of the graft vessel 12, as shown in FIG. 3 of the drawings, and is intended to press the graft vessel 12 into close proximity with the coronary artery 10, during which time suture wire 14 is also pulled upwardly at both outer ends thereof. At that time, a suitable adhesive 26 is applied to the region of contact along distance L wires between the first and second vessels 10, 12. The suture wire 14 may be preferably constituted of a surgical grade stainless steel or similar alloy, and may possess a diameter within the range of about 0.001 to 0.005 inches. During that period of time, blood flow may be maintained in the coronary artery 10. The tool 24 is maintained in the graft vessel 12 so as to apply pressure against the coronary artery 10 during the curing of the adhesive, while concurrently the two outwardly extending strands of the suture wire 14 are pulled upwardly, possibly with the aid of a suitable grasper (not shown). Alternatively, rather than utilizing an adhesive for anastomosis of the first and second vessels 10, 12 to each other, there may be employed methods of manual suturing, staples or other specialized fasteners, as is well known in the medical technology.

Figure 4:
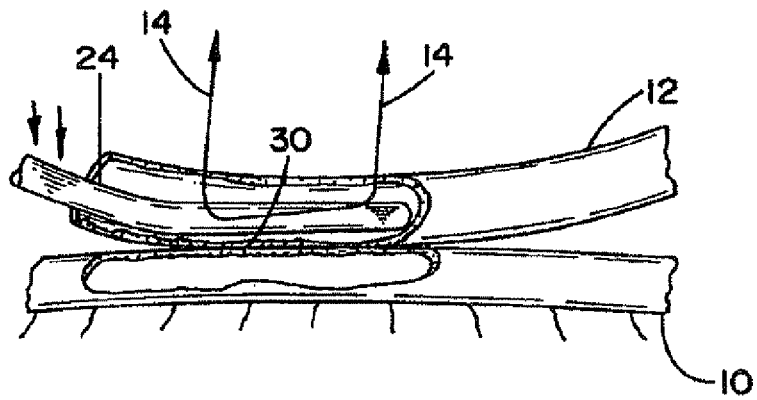

As shown in FIG. 4 of the drawings, subsequent to the curing of the adhesive 26 which has been previously applied so as to adhere together the first and second vessels 10,12 in effect the coronary artery and graft, a fluid flow passageway 30 which is of the length "L" as defined by the distance between the two upwardly extending suture wire portions exiting from vessel 12, is formed in that the wire is utilized to cut an opening or aperture between the joined vessels, such as by reciprocating the wire back and forth until the adjoining walls of the vessels are severed in that region.

Figure 5:
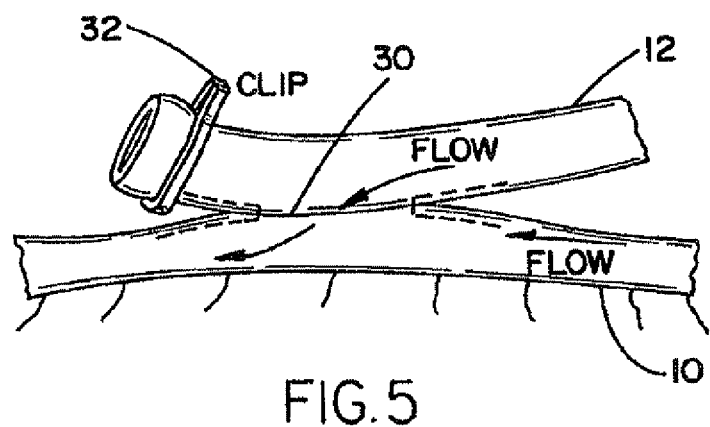

Referring to FIG. 5 of the drawings, a clip 32 may be attached to the open end of the graft or second vessel 12 subsequent to removing the tool 24 therefrom and flow of fluid may be initiated from the second vessel or graft vessel 12 into the coronary artery or target vessel 10 through passageway 30. The moving back and forth of the wire is analogous to the implementation of a so-called "cheese wire" action, during which the tool provides a localized reaction force to the joined vessel walls as the suture wire 14 shears through these walls or vessel tissue. It is also possible to equip the suture wire 14 with an abrasive coating which facilitate the cutting action or sawing through the wall tissue to form the fluid flow passageway 30. Alternatively, the wire may be electrically connected to an electrical surgical generator, whereby minute amount of radio frequency (RF) energy may be controllably applied to the vessel walls to reduce the force needed to cut through. Further embodiments of the foregoing method are described hereinbelow in additional detail.

Subsequent to completing the forming of the flow passageway 30, the suture wire 14 may be withdrawn from the graft vessel 12, leaving only tiny punctures which will readily seal themselves due to normal body mechanisms once blood flow is established in both of the graft and target or coronary vessels.

Pursuant to modified embodiments, as shown in various of the drawing figures, a graft vessel 40 may be attached to the target vessel or coronary artery 10 through an end-to-side anastomosis.

Figure 6:
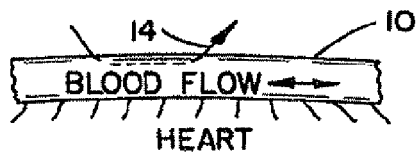
FIGS. 6 through 13 illustrates a modified method for implementing an end-to-end side anastomosis between two vessels, such as a target vessel or coronary artery and a graft vessel.

As shown in FIG. 6 of the drawings, similar to the previous embodiment, the suture wire 14 and needle 16 may be inserted into the coronary artery 10, and egression therefrom so as to form a region of a distance "L" within the vessel 10 which will define the anastomosis with the graft vessel 40. In lieu of needles, contrary to the previous embodiment, the suture wire 14 may have sharpened and rigid end portions, this also being applicable to the preceding embodiment if desired.

Figure 7:
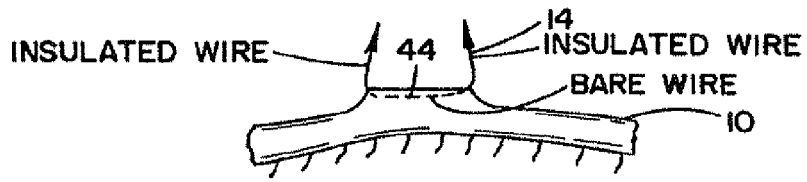
Figure 8:
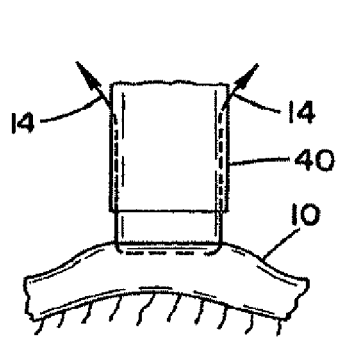

As shown in FIG. 7 of the drawings, the wire 14 may be an insulated wire having a bare wire portion 44 which defines that wire segment which extends interiorly of the coronary artery or first vessel 10. The insulated wire portion which extend outwardly may be color coded, indicating that the bare wire portion is properly positioned within the coronary artery. Similarly, the graft vessel 40 may have an open end positioned over the portion of the coronary or target vessel 10 such that two wire portions extend inwardly of the graft vessel 40 and exit at a height outwardly therefrom by puncturing through the opposite side walls so as to lead these wire portions to the outside of the graft vessel, as indicated in FIG. 8 of the drawings.

Figure 9:
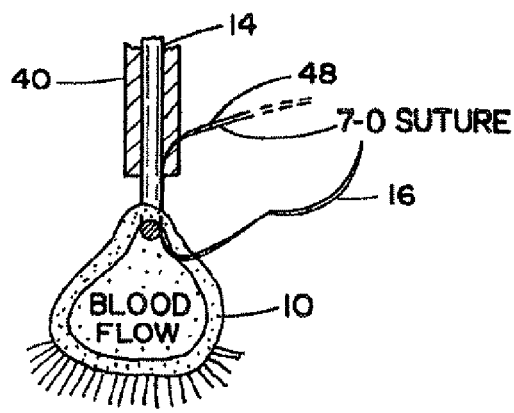

As shown in FIG. 9 of the drawings, the vessels 10 and 40 are drawn towards each other by using or cutting wire 14 to manipulate the vessels from side-to-side, such as for access and visibility. Thereafter, as indicated in the drawing, a conventional suture 48, such as a 7-0 suture, as shown in FIG. 9, may be employed by running suture stitches along the sides of the vessels 10,40 to join these together, with the wire 14 still extending downwardly from the lower end portion of the graft vessel 40 and through the wall of the target coronary artery 10 in which blood flow is still continuing.

Figure 10:
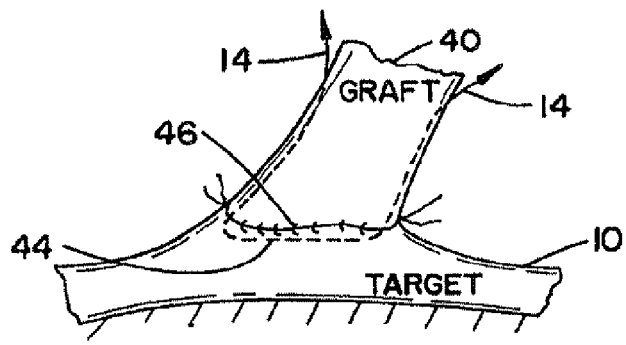
Figure 11:
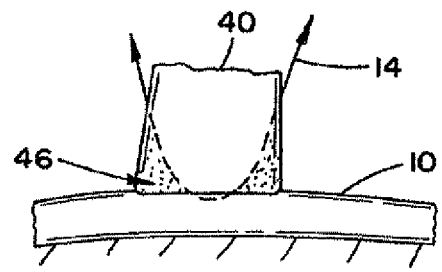
Figure 12:
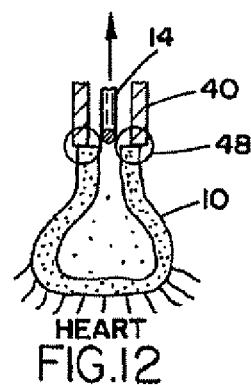
Figure 13:
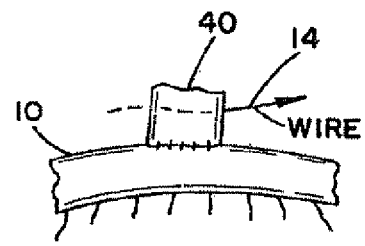

As shown in FIG. 10, the graft vessel 40 has been drawn down until the lower end is in close contact with the surface of the target vessel 10 defined by the wire 14 and as peripherally sutured together. Thereafter, as shown in FIG. 11, subsequent to the suturing and resultant anastomosis of the vessels 10,40 in an end-to-side relationship, an upward force is applied to the wire 14, causing the portion 44 of the wire 14 within the coronary vessel 10 to cut through the wall thereof, as shown specifically in FIG. 12, and to thereby form a blood or fluid flow passageway 46 between the graft vessel 40 and the coronary vessel 10. Thereafter, as shown in FIG. 13 of the drawings, the cutting wire 14 is removed by pulling it out of the graft vessel 40, and the tiny remaining punctures will self seal due to normal body functions and blood flow.

Figure 14:
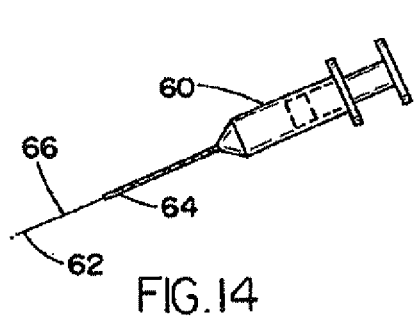
FIG. 14 illustrates, diagrammatically, a device for suturing and gluing the juncture between the vessels in order to implement an anastomosis.
Figure 15:
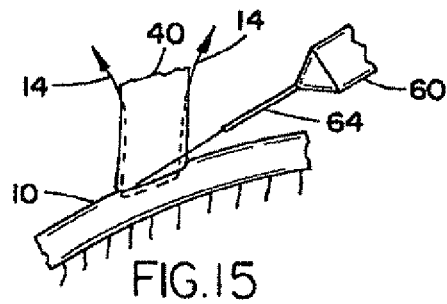
FIG. 15 illustrates a physical application of the device of FIG. 14.
Figure 16:
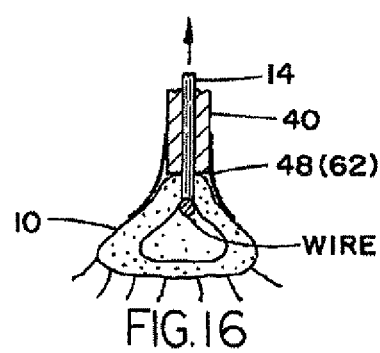
FIG. 16 illustrates an enlarged transverse sectional view through the vessels of FIG. 15.

As shown in FIG. 14 of the drawings, as an alternative to hand suturing with conventional sutures, needles and/or similar anastomosis devices, it is possible to utilize a syringe 60, as schematically indicated, which includes a suture 62 adapted to be expelled in a continuous mode through a cannulated needle 64, concurrently with a suitable adhesive 66, such as a bio-adhesive in the form of cyano-acrylate encompassing or coating the suture. This suture is then "glued" to the adjoining tissue of the vessels 10,40 as shown in FIGS. 15 and 16 of the drawings so as to adhere to the outside wall (adventitia) of the blood vessels 10 rather than being pierced through. Upon contact with the vessel 10 and 40, the sutures 62 will stick and adhere thereto, and a zig zag pattern may be utilized to lay down so-called stitches between the vessels; in effect, producing a glued suture adhering to the outside thereof. Thereafter, as previously, the cutting wire 14 which extends upwardly within the graft vessel and exits the side walls thereof may be pulled up to form a fluid flow passageway 68 between the vessels by shearing through the wall of the coronary artery or target vessel 10 adjacent the graft vessel 40.

Figure 17:
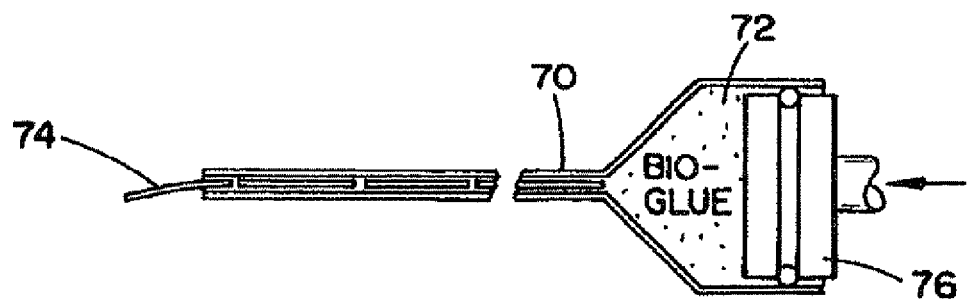
FIG. 17 illustrates a modified device for the performing of the anastomosis between the vessels.
Figure 18:
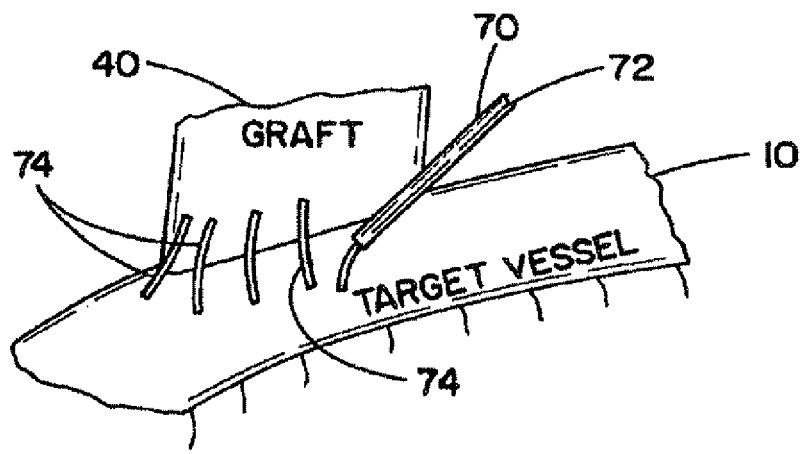
FIG. 18 illustrates the application of sutures and adhesive to the site of the anastomosis as implemented by the device of FIG. 17.
Figure 19:
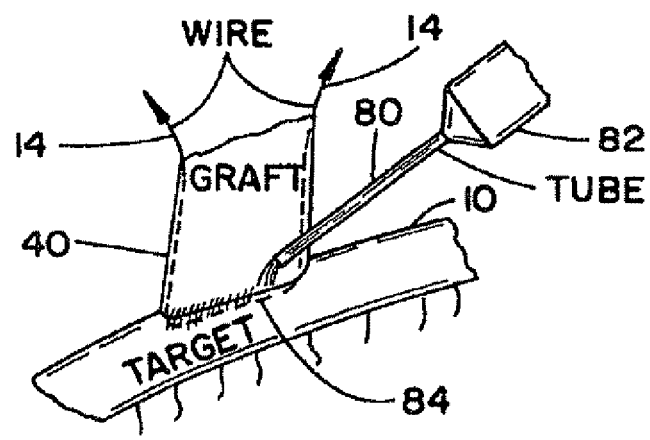
FIG. 19 illustrates an alternative method of implementing anastomosis to the vessels.

A modified version of the foregoing, as shown in FIG. 17 of the drawings, shows that a cannulated syringe 70 may contain a bio-glue in a reservoir 72, and suture segments 74 which are wetted with the bio-glue. By simply pushing a plunger 76, the glue and suture segment 74 are expelled from the orifice of the cannula of syringe 70, and each suture segment positioned on the outer surface of the tissue at the juncture between the coronary artery 10 and the graft vessel 40, where the segments adhere and then the glue cures, as shown in FIG. 18 of the drawings. Consequently, a surgeon can in effect "build" a fabric of sutures on the vessels, which upon the curing of the adhesive will produce an anastomosis. It is also possible that the adhesive be merely brushed onto the outside of the abutting graft and coronary artery vessels 10,40 while the wire 14 is pulled up gently to form a vessel contact. As shown in FIG. 19 of the drawings, by means of a tube 80 having a reservoir 82 of the bio-adhesive, a brush tip 84 may be used for brushing on the adhesive rather than through the added use of any sutures. Subsequent to the curing of the adhesive and drying onto the tissue of the vessels, the wire 14 may be utilized to create the fluid flow passageway between the vessels, in a manner as previously set forth.

Figure 20:
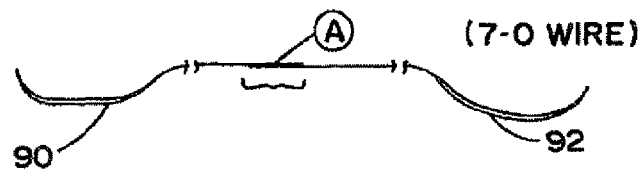
FIG. 20 illustrates a modified construction for the needles and cutting wires.
Figure 21:
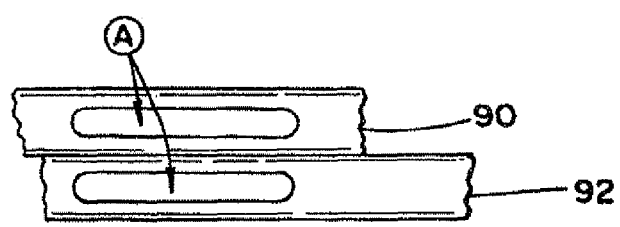
FIG. 21 illustrates an enlarged fragmentary detail of the portion A in FIG. 20.

A modified version of the invention, as shown in FIG. 20 and the enlarged detail in FIG. 21 of area A utilized a pair of wires 90,92 having the central portion thereof, as shown enlarged in FIG. 21, overlapping and superimposed in the region of the juncture between the graft vessel 40 and the coronary artery 10. Each wire which has a needle 94 may be a bipolar conductor wire used to create a passageway in the target vessel 10 in fluid flow relationship with the graft vessel 40. In this instance, the concept resides in isolating the energy transfer, in effect, cutting of the tissue at that portion of the target vessel which is to be opened to the graft vessel 40.

The two wires are electrically insulated from each other through the application of lacquer, polymers or other insulations, in combination with the bi-polar energy.

Figure 22:
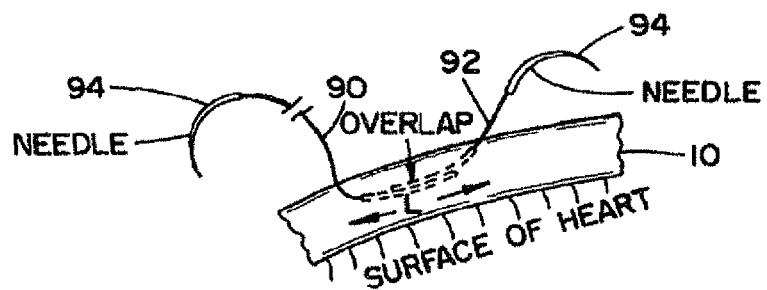
FIG. 22 illustrates the utilization of the wires shown in FIGS. 20 and 21.
Figure 23:
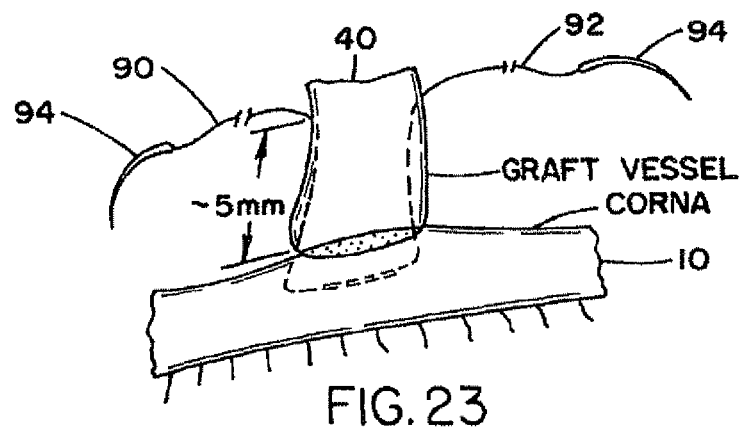
FIG. 23 illustrates the positioning of the graft vessel and juncture with the coronary artery utilizing the wires of FIG. 22.

Utilizing a special two bipolar tweezer to supply an entry to the wire and to manipulate the wires during anastomosis enables the exposed metal wire portions which are formed by the overlapped wire portions, which have any insulation scraped off after dipping in insulating material etc., and bonding together, as shown in FIG. 22, to be inserted into the coronary artery 10 whereby the overlapping portion form the length L which is to eventually provide the flow passageway with the graft vessel 40. Thereafter, as shown in FIG. 23, a graft vessel 40 is attached in an end-to-side relationship to the coronary artery 10, as previously described, and tensioned by means of the wire 90, 92 being pulled transversely as then exist through the side walls of the graft vessel 40 at a distance above the location of the juncture with the coronary artery 10.

Figure 24:
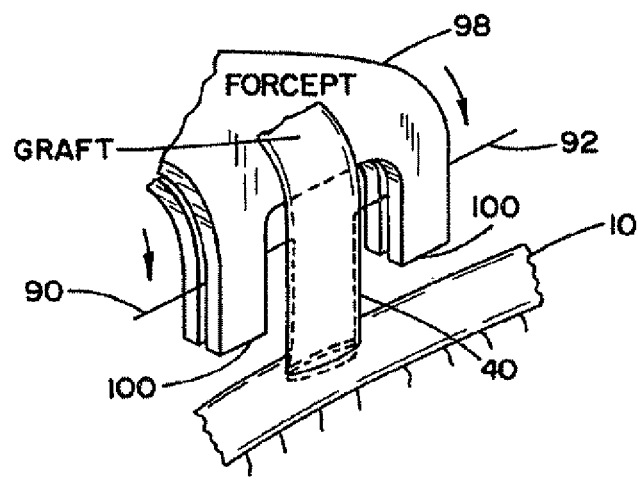
FIG. 24 illustrates a perspective view of the front portion of an instrument for applying energy to the wires in order to provide the cutting operation to form the fluid flow passage between the vessels; after anastomosis thereof.

As shown in FIG. 24 of the drawings, a leading or operative tip portion of a forceps 98 may have two-tine construction, whereby bipolar energy is used to clamp onto the bare wire near each side of the graft vessel 40. By pushing the forceps down towards the target artery 10, the graft vessel 40 is abutted against the artery while the target artery is then tented inside the lumen of the graft vessel. Joining means for anastomosis are applied while this position of the vessels is maintained, such as previously described through glues, fasteners, sutures or the like. Fasteners are applied at each side whereby the forceps abut the vessels with each other.

Figure 25:
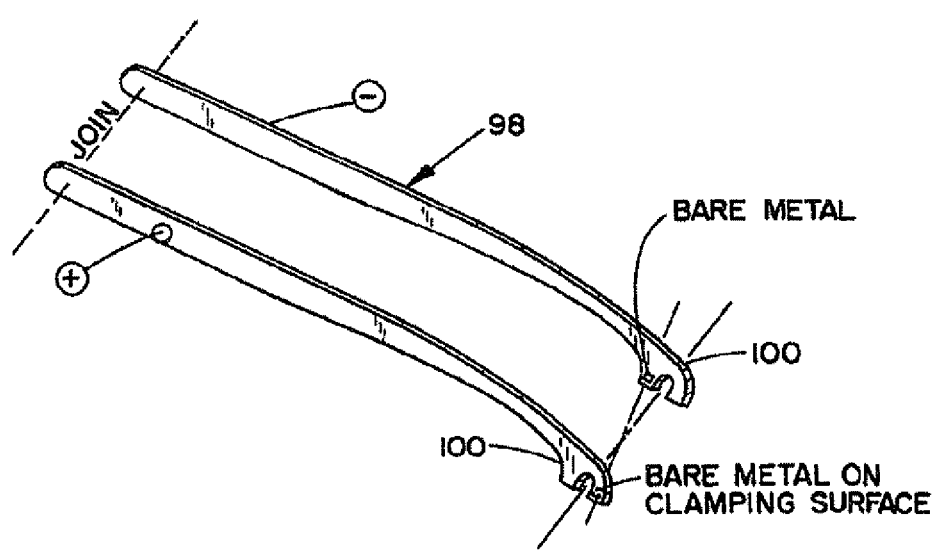
FIG. 25 illustrates an exploded perspective detail of the device of FIG. 24.
Figure 27:
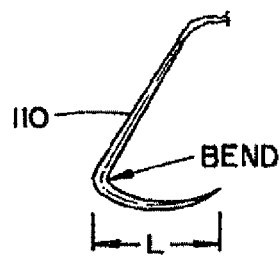
FIGS. 27 through 30 illustrate steps in utilizing a different type of suture and hooked needle structure to provide the anastomosis.

Thereafter, as shown in FIG. 25 of the drawings where the perspective view of the forceps shows the bare metal leading tine portions thereof on the clamping surface the forceps, electrically connect the wires 90,92 to a bipolar energy source (not shown). The portion of the wires clamped by the forceps are either uninsulated or any insulation is removed as the forceps are clamped onto them, such as possibly due to abrasion, teeth or other stripping surfaces provided on the clamps. The forceps are opened and closed by trigger action at an opposite proximal end, or a conventional trigger grip may be employed. One side of the forceps may be electrically negative and the other side positive, with an insulating barrier provided therebetween.

Figure 26:
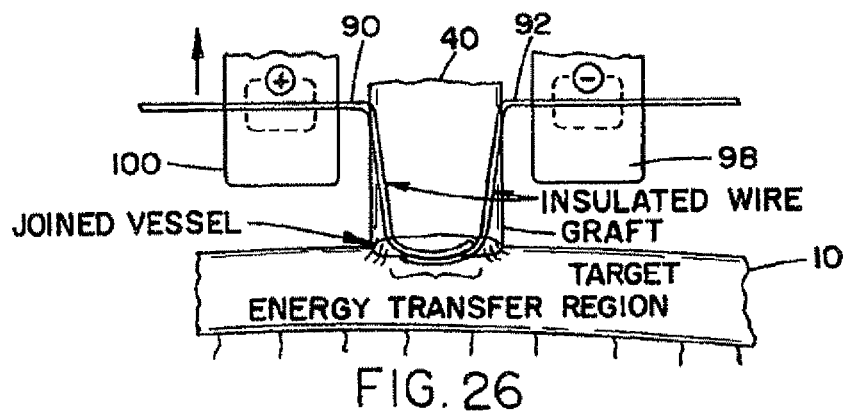
FIG. 26 illustrates a general diagrammatic representation of the utilization of the device shown in FIGS. 24 and 25 for forming the passageway between the target and graft vessels subsequent to implementing anastomosis.

As shown in FIG. 26 of the drawings, when the vessels 10,40 are joined together, then the forceps tines 100 which are clamped onto the wires 90,92 are pulled in a proximal direction and the bipolar energy is "pulsed" by an electrical current provided for through an external control. A fluid flow passageway is thus created between the target vessel 10 and the graft vessel 40, and the wires are then pulled up into the graft vessel 40. The forceps is then removed form the wires, and then one end of the wire is pulled out from the graft vessel to extract the wires therefrom. The punctures created in the graft vessel are basically tiny punctures which are self occluding, and the blood circulation is restored to the graft vessel 40 which is now in fluid flow communication with the target vessel or coronary artery 10.

Figure 28:
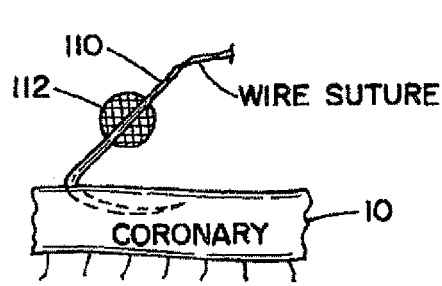
Figure 29:
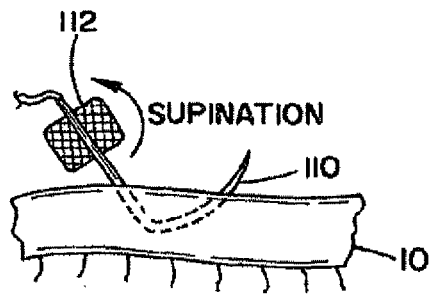
Figure 30:
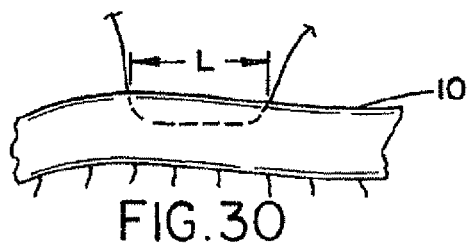

Alternatively, as shown in FIGS. 27 through 30 of the drawings, hooked needles 110 may be provided which have a leading hooked end of a length L adapted to form the length of the passageway by hooking into the coronary artery 10 at a first location as shown in FIG. 28, and then rotated by means of a suitable cradle holder 112 so as to egress at a second location forming two punctures at a distance L. Thereafter, the suture wire attached to the needle are used in the process of attaching a coronary artery to the graft vessel as hereinbefore in the manner as described.

Figure 31:
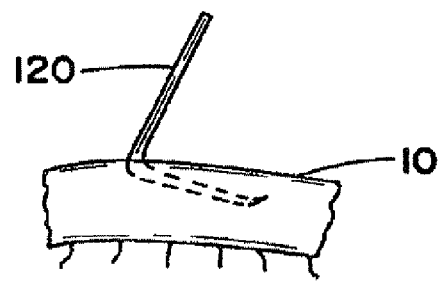
FIGS. 31 through 33 illustrate steps in alternatively utilizing a hooked needle portion to provide the require anastomosis, and for thereafter forming the passageway between a target vessel and graft vessel.
Figure 32:
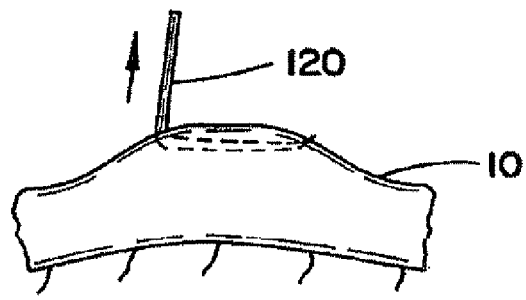
Figure 33:
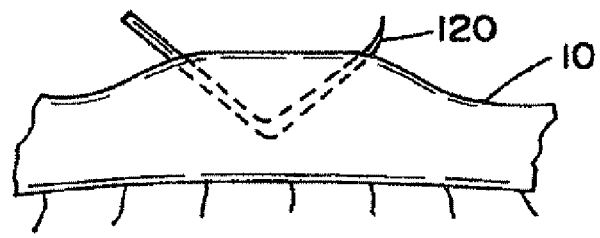

As an alternative to the hooked needle 110, there can be also provided an L-shaped needle 120 as shown in FIGS. 31 to 33, wherein the needle has a length L and is adapted to be pulled upwardly so as to pierce the coronary artery wall at locations equal to the length of the intended passageway portion L which is to form the opening in fluid flow communication with the graft vessel 40. This is similar to the function of the needle structure described with regard to FIGS. 27 to 29, and the attachment of the graft vessel 40 to the coronary artery 10 may then be implemented in any manner as described hereinbefore. The foregoing clearly provides unique methods and apparatus for attaching a graft vessel to a target vessel such as a coronary artery while permitting a continuous blood flow through the latter and then enabling the anastomosis of the vessels prior to the formation of the fluid flow passageway therebetween.

While the invention has been particularly shown and described with respect to preferred embodiments thereof; it will be understood by those skilled in the art that the foregoing and other changes in form and details may be made therein without departing from the spirit and scope of the invention.

What is claimed is:

1. A method for implementing a vascular anastomosis between a graft vessel and a target vessel and creating a fluid flow passageway therebetween, said method comprising:
   puncturing the wall of the target vessel at a first location to insert an end of a wire into the target vessel;
   puncturing the wall of the target vessel at a second location distanced from the first location to allow the end to exit the target vessel;
   defining a region of contact on the wall of the target vessel between the first location and the second location;
   attaching the graft vessel to the target vessel adjacent the region of contact; and
   providing a fluid flow passageway extending through the region of contact to allow fluid communication between the lumens of the target vessel and the graft vessel.

2. The method of claim 1, wherein attaching the target vessel with the graft vessel further comprises applying a curable adhesive to the vessels.

3. The method of claim 1, wherein attaching the target vessel with the graft vessel further comprises stitching sutures about a periphery of the region of contact to secure the target vessel with the graft vessel.

4. The method of claim 1, wherein attaching the target vessel with the graft vessel further comprises applying a glue-coated suture whereat the target vessel and the graft vessel are in contact.

5. The method of claim 4, wherein applying the glue-coated suture further comprises providing a cannulated syringe whereby a plurality of glue-coated sutures are successively applied to secure the vessels to each other.

6. The method of claim 1, wherein applying the glue-coated suture further comprises applying a bio-adhesive.

7. The method of claim 6, wherein the bio-adhesive is cyano-acrylate.

8. The method of claim 1, wherein providing the fluid flow passageway comprises reciprocating the wire to cut through at least the wall of the target vessel in the region of contact.

9. The method of claim 8, wherein the wire includes an abrasive surface to assist in cutting through vessel walls.

10. The method of claim 1, wherein providing the fluid flow passageway comprises cutting through the walls in the region of contact of the target vessel and the graft vessel, which are in side-to-side contact with one another.

11. The method of claim 1, wherein providing the fluid flow passageway comprises cutting through at least the wall of the target vessel in the region of contact of the target vessel and the graft vessel, which are in end-to-side contact with one another.

12. The method of claim 1, wherein providing the fluid flow passageway comprises providing an insulated electrically-conductive wire having an uninsulated portion extending within the target vessel in the region of contact, and imparting electrical energy to the wire.

13. The method of claim 1, wherein providing the fluid flow passageway comprises electrically energizing the wire to cut through at least the wall of the target vessel in the region of contact.

14. The method of claim 1, wherein providing the fluid flow passageway comprises supplying the wire with RF energy to cut through at least the wall of the target vessel.

\* \* \* \* \*